United States Patent [19]

Tsao

[11] Patent Number: 5,252,291
[45] Date of Patent: Oct. 12, 1993

[54] MULTI-ELECTRODE CONTACT LENS DISINFECTION AND CLEANING DEVICE AND METHOD THEREFOR

[75] Inventor: Mark F. Tsao, Lawrenceville, Ga.

[73] Assignee: Ciba Geigy Corporation, Ardsley, N.Y.

[21] Appl. No.: 909,672

[22] Filed: Jul. 7, 1992

[51] Int. Cl.$^5$ .......................... A61L 2/02; A61L 2/16
[52] U.S. Cl. .......................... 422/23; 422/28; 422/29; 422/37; 422/292; 422/300; 422/301; 134/901; 204/412
[58] Field of Search .............. 422/292, 23, 28, 29, 422/37, 293, 300, 301; 134/1, 10, 26, 27, 42, 57 R, 901; 204/130, 412

[56] References Cited

U.S. PATENT DOCUMENTS

| | | |
|---|---|---|
| 3,627,133 | 12/1971 | Rak ........................ 210/98 |
| 3,660,261 | 5/1972 | Wright et al. .............. 204/98 |
| 4,202,740 | 5/1980 | Stoner et al. .............. 204/130 |
| 4,289,599 | 9/1981 | Fushihara ................. 204/275 |
| 4,316,787 | 2/1982 | Themy .................... 204/242 |
| 4,512,865 | 4/1985 | Yamauchi ................. 204/271 |
| 4,732,185 | 3/1988 | Cowle et al. .............. 134/84 |
| 4,839,004 | 6/1989 | Castellini ................ 422/37 X |
| 4,872,965 | 10/1989 | Pankow ................... 204/299 R |
| 4,921,544 | 5/1990 | Cowle et al. .............. 134/1 |
| 4,997,626 | 3/1991 | Dziabo et al. ............. 422/28 X |

FOREIGN PATENT DOCUMENTS

| | | |
|---|---|---|
| 0441389 | 8/1991 | European Pat. Off. . |
| 63-254416 | 10/1988 | Japan . |
| 2200653 | 8/1988 | United Kingdom . |
| 8900430 | 1/1989 | World Int. Prop. O. . |

Primary Examiner—Robert J. Warden
Assistant Examiner—E. Leigh Dawson
Attorney, Agent, or Firm—Wenderoth, Lind & Ponack

[57] ABSTRACT

A contact lens care device and method for cleaning and disinfecting contact lenses. The invention utilizes both principles of electrophoresis and electrolysis. The device uses a halide-containing electrolytic buffer solution for disinfecting and cleaning. A halogen concentration is generated electrolytically from the halide in the contact lens containing well by the generation of an electrical field between the two electrodes disposed in the well. The field is maintained for a time sufficient to generate a concentration of halogen which can disinfect the lens. The lens is cleaned electrophoretically at the same time. Then, the conversion of the halide to halogen is reversed to remove the halogen from the contact lens containing well. This is done by generating an electrical field between the well electrodes and another electrode located in a reservoir connected to the well by a narrow channel or inert divider. The elimination of halogen is so complete that the lens does not need to be rinsed before insertion in the eye. The device may include an automatic control means.

25 Claims, 6 Drawing Sheets

MULTI-ELECTRODE CONTACT LENS DISINFECTION AND CLEANING DEVICE AND METHOD THEREFOR

BACKGROUND OF THE INVENTION

1. Field of the Invention

The present invention relates to a contact lens care system for cleaning and disinfecting contact lenses, and to the method therefor. More particularly, the contact lens care system is a multi-electrode device which utilizes the principles of electrolysis and electrophoresis to both disinfect and clean contact lenses.

2. Description of the Related Art

It is particularly important that so-called soft contact lenses be kept sterile, because they tend to cause infections in the eye if they are not periodically disinfected.

Past methods of disinfecting such lenses have involved such cumbersome steps as boiling them for a predetermined length of time, or immersing them in a disinfecting solution, particularly hydrogen peroxide solutions. The latter method also requires immersing the lenses in a neutralizing or rinsing solution to remove the disinfecting solution from the lenses, because this solution can be highly irritating to the eye.

These methods suffer from various drawbacks, for example the lens disinfection unit may be cumbersome to use, since it may require the insertion and removal of the lens holder several times during the course of the process. Additionally, the user may forget to neutralize the lenses after disinfection, or confuse the disinfecting and rinsing solutions with one another, since both solutions are usually clear solutions. Needless to say, it is extremely dangerous to insert into one's eye a contact lens which has not had the disinfecting solution entirely removed.

Contact lenses must also be cleaned to remove contaminants from the lenses such as proteinaceous substances, and methods for cleaning contact lenses to remove these substances include the immersion of the lenses in surface active agents (i.e. soaps), enzymes, etc. These methods typically require that the cleaning solution be rinsed from the lenses, and the methods typically do not accomplish a satisfactory disinfection of the lenses.

Methods for cleaning contact lenses using an electrophoretic system have been known, such as those described in U.S. Pat. Nos. 4,921,544 and 4,732,185, however these methods have not proved to be completely satisfactory. These methods involve the immersion of the contact lenses in a buffer solution, and the creation of an electric field in the solution by a pair of spaced electrodes. Contaminants on the lenses such as proteins become charged and are attracted to the oppositely charged electrode, thereby cleaning the lenses.

Some drawbacks to these methods are that in order to disinfect the lenses, a disinfecting agent is typically required to be added to the buffer solution. As in the above-described methods, the disinfecting agent must be neutralized or rinsed from the lenses before insertion into the eye. Other drawbacks are, for example, that protein may be accumulated on the electrodes during electrolysis, and that a lengthy disinfection time may be needed.

Methods for disinfecting contact lenses using an electrolytic system have been known, such as proposed in Japanese Patent Publication No. 60-2055, however these methods have not proved entirely satisfactory. These methods involve the creation of a disinfecting solution by the electrolysis of a saline solution to produce chlorine ($Cl_2$). Such methods are ineffective in completely removing proteinaceous materials from the contact lenses so that surface active agents, enzymes, etc. are typically needed to clean the lenses. The lenses must also be rinsed at the completion of that type of disinfecting process before insertion in the eye of the wearer to remove the chlorine.

Other known methods for cleaning contact lenses using the principle of electrolysis include the method proposed in Japanese Patent Publication 63-254416. That method uses a multi-electrode device which cleans contact lenses by the electrolysis of a physiologic saline solution to produce a high pH solution in the well containing the contact lenses. The highly alkaline solution dissolves the proteinaceous substances on the lenses, and an ultrasound cleaning device is used to help remove these substances from the lens surfaces. After cleaning of the lenses, the alkaline solution is then neutralized by reversing the polarity of the electrodes, thereby avoiding the need of rinsing or neutralizing the alkaline solution on the lenses before insertion in the eyes. This method does not disinfect the contact lenses.

SUMMARY OF THE INVENTION

It is an object of the present invention to provide an improved contact lens care system and method for both cleaning and disinfecting contact lenses, which method is simple and easy to use and overcomes the above-described disadvantages of known methods and devices for cleaning and disinfecting contact lenses.

More particularly, it is an object of the invention to provide a contact lens care system which can both clean and disinfect contact lenses, and which can then neutralize the cleaning and disinfecting solution used, so that the lenses may be immediately placed in the eyes of the wearer after cleaning and disinfecting without the need for any rinsing of the lenses.

It is a further object of the invention to provide a contact lens care system and method which can accomplish cleaning and disinfecting of contact lens without the need to digitally clean the lenses (i.e. by hand); without the need to change the solution; without the need to add any additional chemicals to the solution; and without the need to insert and remove the lenses in the device several times during the process.

With the foregoing objects in mind, the contact lens care system of the present invention will be briefly described, after which the contact lens care system will be described in detail hereinbelow with reference to the preferred embodiments of the invention.

The contact lens care system of the present invention is a multi-electrode device comprising a housing having one or two wells which serve as cavities for holding the contact lenses and for immersing the contact lenses in the cleaning and disinfecting solution. Regardless of whether one or two lens wells are provided, each lens well is provided with two opposing electrodes spaced apart from each other for inserting one or two contact lens or lenses therebetween. When one lens well is provided, the opposing electrodes are preferably spaced apart for receiving two contact lenses therebetween, so that two lenses may be cleaned at the same time. The opposing electrodes in such a single well may be spaced apart for receiving and cleaning only a single contact lens, but such system has the disadvantage of only being capable of cleaning a single contact lens at a time. On the other hand, when two lens wells are provided, the opposing electrodes may be spaced apart for receiving a single contact lens therebetween, thereby two contact lenses may be cleaned at the same time using this design.

The contact lens or lenses are placed in the lens well between the opposing electrodes. Preferably, a lens holding means is provided for holding the contact lens or lenses in the well between the electrodes. The surfaces of the opposing faces of the electrodes which face the contact lens may be adapted to serve as the lens holding means, for example by configuring the shape of the opposing faces of the electrodes into complementary convex and concave configurations, adapted to the shape of the curved contact lens. In this case, the opposing electrodes are preferably spaced apart for receiving a single contact lens. Alternatively, the lens holding means may be a lens basket for holding one or two contact lenses in a spaced apart arrangement. In this case, the opposing electrodes are spaced apart for receiving the lens basket therebetween.

In addition to the lens wells, the housing of the device is provided with another cavity for holding the disinfecting and cleaning solution. This cavity or reservoir has at least one electrode.

The lens well or wells are connected to the reservoir by an ion permeable bridge such as a narrow channel, a porous inert divider, an ion permeable membrane, or any other conventional structure which functions as a salt bridge. If two lens wells are provided, the two lens wells may also be connected to each other so that the cleaning and disinfecting solution in the two lens wells may communicate. Alternatively, the lens wells may be isolated from each other so that the cleaning and disinfecting solution may not communicate between the wells except through the reservoir.

If a narrow channel is used as the ion permeable divider, it is desirable that the channel between the lens well or wells and the reservoir be completely filled with the disinfecting and cleaning solution, so that air bubbles in the channel can be minimized, and so that the most effective salt bridge may be established between the lens well or wells and the reservoir. In order to accomplish this object, the present invention utilizes a novel method for filling the lens well or wells and the channel with the disinfecting and cleaning solution.

That is, the reservoir is first filled with the disinfecting and cleaning solution to a predetermined level. A solution displacement block, adapted to fit into an upper portion of the reservoir, is then inserted into the reservoir. The solution displacement block forces a predetermined amount of cleaning and disinfecting solution from the reservoir through the channel into the lens well or wells. The predetermined amount of solution forced into the lens well or wells is sufficient to totally immerse the opposing surfaces of the electrodes and the contact lens inserted therebetween. And, due to the location of the channel opening and the electrode in the reservoir, the level of disinfecting and cleaning solution which remains in the reservoir after insertion of the solution displacement block is sufficient to immerse the channel opening and the reservoir electrode, thereby allowing for electrolytic reactions to occur at the electrode, and thereby allowing for ion communication between the reservoir and the lens well or wells through the channel.

The device of the present invention also includes a control means, operatively connected to the electrodes of the lens well or wells and the reservoir. The control means permits the control of the polarity of each electrode and the amount of potential voltage applied to each electrode. Preferably the control means is automatic and controls the electrode polarity and potential voltage according to a predetermined program. Preferably, the control means also includes a timing means for automatically controlling the length or duration of the polarity and the potential applied to each electrode.

Thus, the lens care system of the present invention is effective in both cleaning and disinfecting contact lenses using the principles of electrolysis and electrophoresis. The following is a summary of the cleaning and disinfecting process.

The disinfecting and cleaning solution used in the lens care system of the present invention may be any halide-containing electrolytic buffer solution. Examples of preferable electrolytic buffer solutions are borate, phosphate or other physiologically compatible buffer saline solutions. Examples of preferable halide compounds are NaCl, KCl, NaBr and KBr.

The contact lens or lenses are placed in the lens holding means of the lens well or wells of the device. The lens well or wells and the reservoir are filled with disinfecting and cleaning solution according to the above-described process. The device is then turned on by the user.

In a first step, opposite electrical potentials are applied to the opposing electrodes in the well or wells by action of the control means, causing the two opposing electrodes to exhibit opposite polarities. No potential need be applied to the reservoir electrode during this initial step.

An electric field is established between the oppositely charged electrodes in the electrolytic buffer solution of the well or wells. The electric field generated causes contaminants on the contact lenses to become charged and attracted to the oppositely charged electrode, thereby cleaning the lenses electrophoretically.

At the same time, the opposite electric potentials applied to the opposing electrodes causes an electrolytic reaction to occur in the halide-containing electrolytic buffer solution at the positive and negative electrodes.

At the positive electrode, the halide in the buffer solution, for example $Cl^-$, which is likely in salt form such as NaCl, is converted to the halogen form $Cl_2$. The reaction taking place at the surface of this electrode is:

$$NaCl \rightarrow \tfrac{1}{2}Cl_2 + Na^+ + e^-$$

Other reactions taking place at the positive and negative electrodes have essentially no effect on the pH of the solution due to use of the electrolytic buffer solution.

The first step is continued for a sufficient length of time, at the particular electric potentials applied to the electrodes, to disinfect and clean the lenses of contaminants.

Then, in a second step, the polarity of the electrodes is changed. A positive charge is applied to the reservoir electrode, and a negative charge is applied to both opposing electrodes in the lens well or wells.

The second step has the effect of reversing the electrolytic reaction which forms the halogen $Cl_2$ from the halide. During this step, the halogen is converted back to its halide salt form. The surfaces of the lens well electrodes are also cleaned of contaminants during this polarity changing process.

The second step is continued for a sufficient length of time to eliminate or at least reduce the concentration of halogen in the lens well or wells to such an amount that no rinsing of the lenses is necessary before insertion of the lenses into the eye of the wearer.

The foregoing constitutes a summary of the lens care system of the present invention. By way of example, the preferred embodiments of the present invention will be described with reference to the accompanying drawings, in which:

Figure 1A:
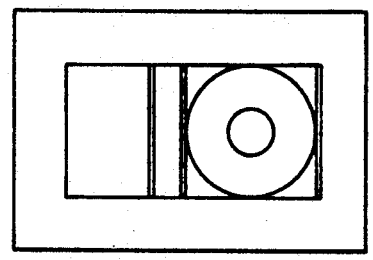
FIGS. 1A-D are illustrations of a first embodiment of the contact lens care system of the present invention having a reservoir and a single lens well.
Figure 1D:
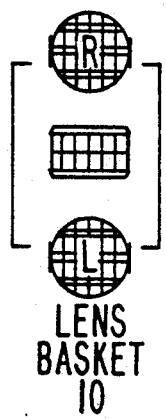
Figure 1B:
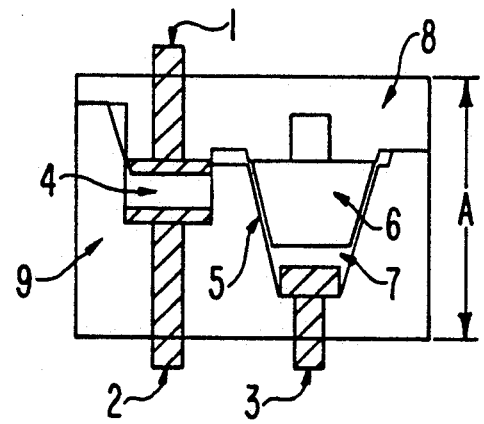
Figure 1C:
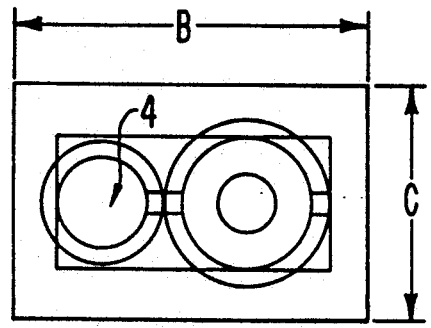

The unit of measurement shown in the drawings is inches.

DETAILED DESCRIPTION OF THE PREFERRED EMBODIMENTS

Referring to FIGS. 1A-D, a preferred device of the present invention is shown which comprises a housing 9 and a top 8 which may be made out of any conventional non-electrical conducting material.

The housing 9 contains one lens well 4 for immersing the contact lens and a reservoir 7. The lens well 4 and reservoir 7 are connected by a narrow channel 5 made of a conventional material. A solution displacement block 6 fits into the upper portion of the reservoir.

The lens well 4 contains two opposing electrodes 1,2 for generating an electric field therebetween. The two lens well electrodes 1,2 are spaced apart for placing the contact lenses therebetween. In this embodiment, the contact lenses are held in a contact lens basket.

The electrodes 1,2 need not be spaced apart any specific distance, however the closer the distance the opposing electrode surfaces are spaced to each other, the less time is generally required to generate a disinfecting concentration of halogen in the well, and the less time is required to neutralize the halogen. Preferably, the electrodes are spaced apart a distance of about 3/16's of an inch or so, which allows a very short time period to be required to generate and neutralize the halogen concentration.

In this embodiment using a lens basket, the distance between the electrodes must be greater and is dictated by the size of the lens basket.

The reservoir 7 has one electrode 3 in this embodiment. A reservoir is not limited to one electrode and may have two or more electrodes.

The electrodes are comprised of a conventional inert electrically conductive material, e.g. platinum, graphite, palladium, etc., or a conductive polymer.

The upper electrode may be integrally connected to the top 8 of the device. Preferably, the top 8 is hinged to the housing so that the electrical connection between the upper electrode and the rest of the device is protected.

In this embodiment, the opposing surfaces of the two opposing well electrodes are flat to accomodate a lens basket 10. The lenses may be held in the lens basket 10 in any orientation but it is preferable that the lenses be oriented in a horizontal direction one over the other. The lens basket may be of the conventional type which hold two lenses in separate side by side compartments and which have separate openings marked with an indication of which lens (left or right) is placed in the respective compartment.

In addition to the above-described features, the device must have a means for operatively connecting the electrodes to a power source, e.g. a DC power source. This is not specifically shown in the figures.

Also not shown is the control means of the device, which preferably is a control or programming unit for automatically controlling the electrode polarity and potential of the electrodes, as well as the timing and duration of the process steps, so that the optimum disinfection and cleaning efficacy is obtained.

Figure 2A:
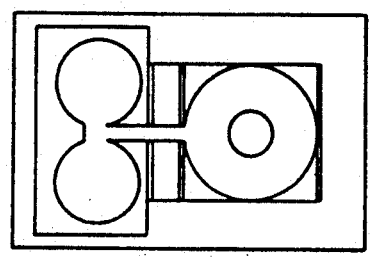
FIGS. 2A-C are illustrations of a second embodiment of the contact lens care system of the present invention having a reservoir and two lens wells.
Figure 2B:
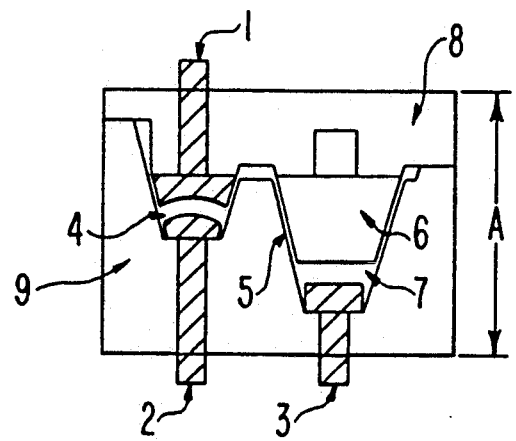
Figure 2C:
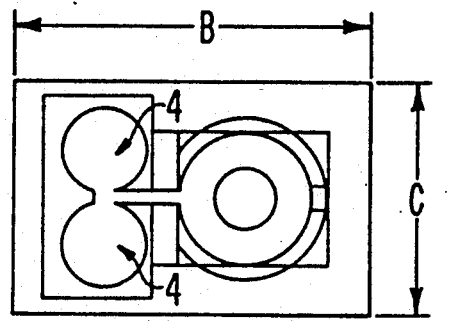

Referring to FIGS. 2A-C, a second preferred embodiment of the present invention is shown which has two lens wells 4 which are connected so that the electrolytic buffer solution may intermix.

The opposing surfaces of the lens well electrodes are complementary concave and convex configurations for placing a lens therebetween. The surfaces of the lens well electrodes are preferably spaced apart about 3/16's of an inch or so in order to minimize the time required to complete the disinfecting and cleaning process.

Figure 3A:
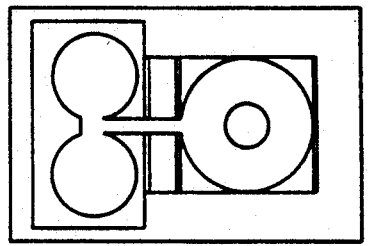
FIGS. 3A-C are illustrations of a variation of the second embodiment shown in FIGS. 2A-C showing a different well electrode structure.
Figure 3B:
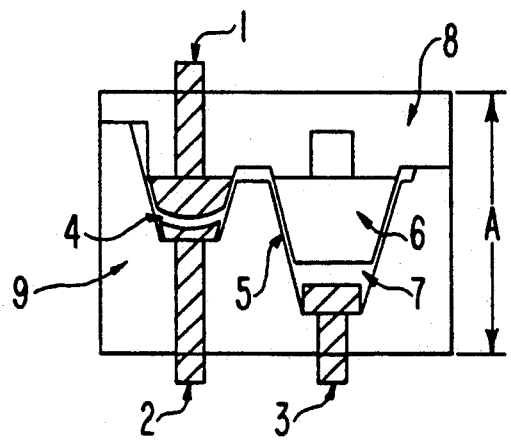
Figure 3C:
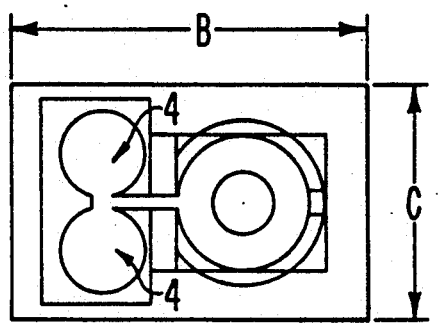

Referring to FIGS. 3A-C, a variation of the second preferred embodiment is shown, in which the lens well electrodes have a configuration which is a mirror image to those shown in FIGS. 2A-C.

Figure 4A:
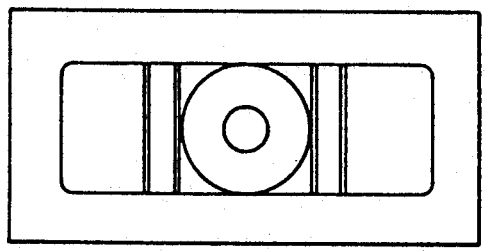
FIGS. 4A-C are illustrations of a third embodiment of the contact lens care system of the present invention having a reservoir and two lens wells.
Figure 4B:
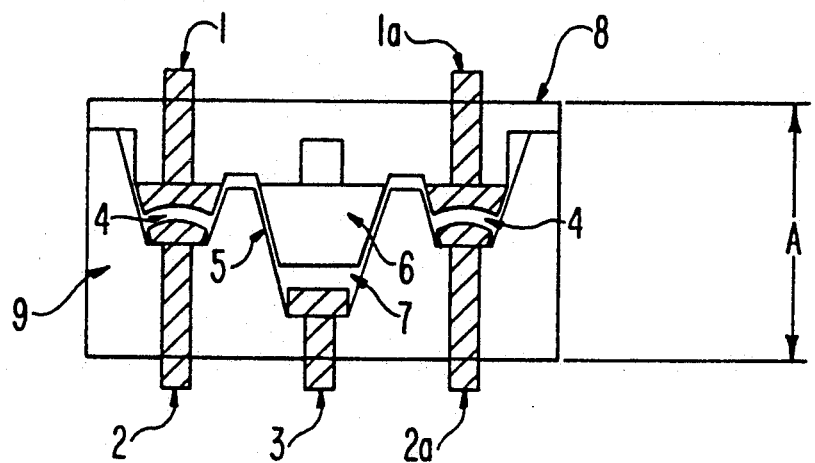
Figure 4C:
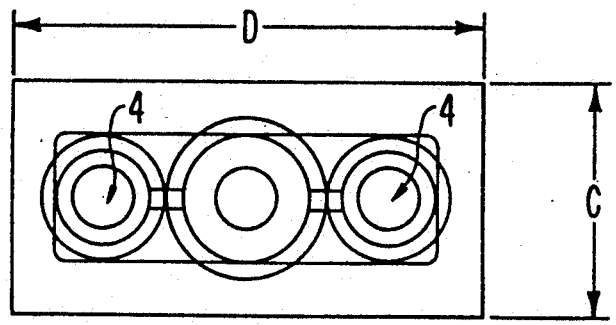

Referring to FIGS. 4A-C, a third preferred embodiment is shown having two lens wells 4 which are isolated from each other so that the electrolytic buffer solution in the lens wells may not intermix.

Figure 5A:
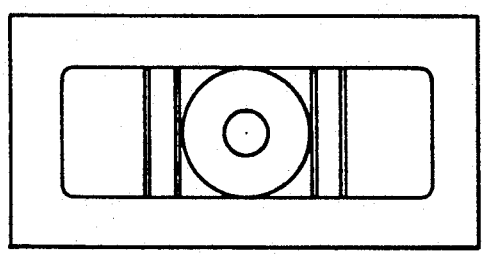
FIGS. 5A-C are illustration of a variation of the third embodiment shown in FIGS. 4A-C showing a different well electrode structure.
Figure 5B:
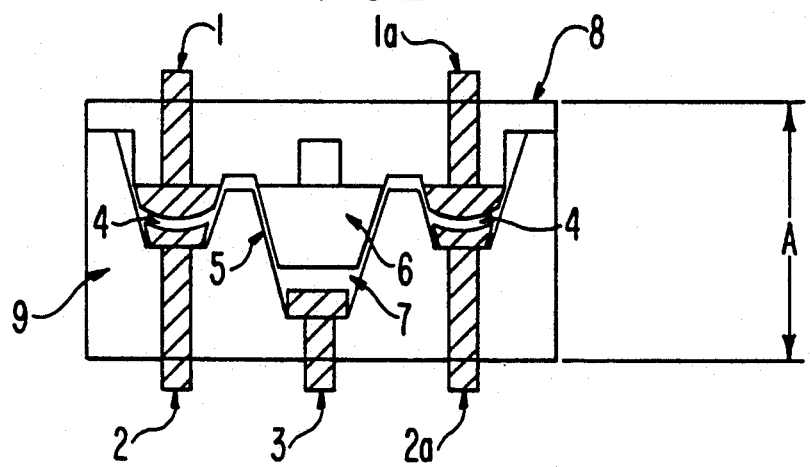
Figure 5C:
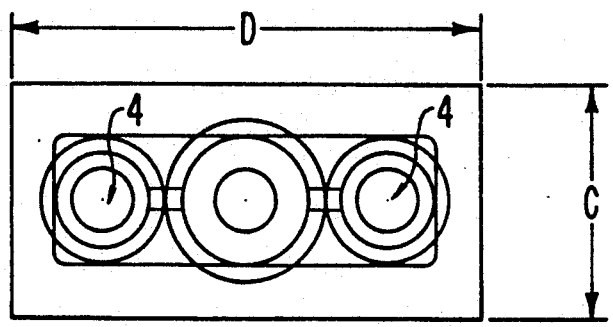

Referring to FIGS. 5A-C, a variation of the third preferred embodiment is shown, in which the well electrodes have the opposite configuration to those shown in FIGS. 4A-C.

Figure 6A:
FIGS. 6A-B are illustrations of the control unit and housing unit in the form of separate units which are connected to each other by a cable or an interlocking arrangement.
Figure 6B:
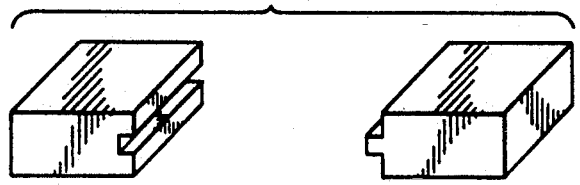

Referring to FIGS. 6A-B, the control unit may be a separate unit from the housing unit and they may be connected to each other by cable or an interlocking socket arrangement. Alternatively, the control unit may be permanently incorporated in the housing unit.

Figure 7A:
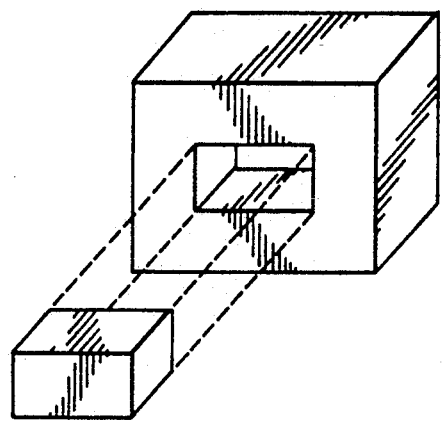
FIGS 7A-B are illustrations of the control unit and housing unit in the form of separate units, wherein the housing unit is removably insertable into the control unit.
Figure 7B:
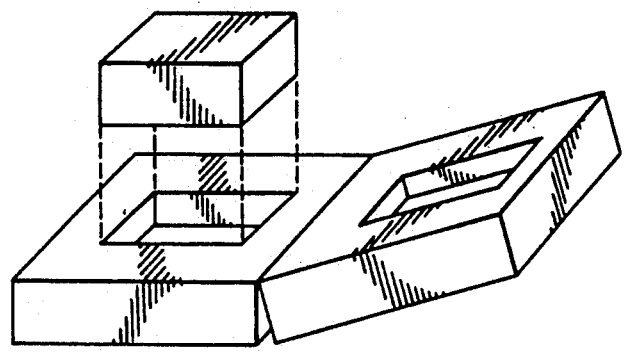

FIGS. 7A-B shows another embodiment of the control unit and the housing unit as separate units, in which case the housing unit is insertable into and removable from the control unit, for example as illustrated in FIGS. 7A-B. Alternatively, the control unit may be insertable into and removable from the housing unit.

In referring to the control and housing units above, the term "control unit" means a unit containing the electronic circuitry for operatively connecting the electrodes with the power source and for controlling the polarity of the electrodes. The control unit may optionally contain a power pack (AC or DC battery), an automatic switching mechanism, indicator means, etc. The term "housing unit" means a unit containing the lens wells, reservoir, electrodes, lens baskets, etc.

The device may be designed so that it is turned on by the user using a hand-operated switching device. Alternatively, the device may be automatically activated, for example, upon the insertion of the housing unit into the control unit (embodiment of FIGS. 7A-B), or the connection of the housing unit with the control unit (embodiment of FIGS. 6A-B), or upon closing of the top 8 of the device (such as in embodiment of FIGS. 1A-D).

The method of the present invention for cleaning and disinfecting contact lenses will now be explained in detail.

The present method comprises immersing a contact lens or lenses in a halide-containing electrolytic buffer solution which is contained in a well having two spaced apart electrodes. The electrodes and lens holding means are adapted to expose the surface of the contact lenses inserted therebetween to the disinfecting and cleaning solution.

The lens or lenses are placed by the user of the device in the lens holding means between the opposing surfaces of the two lens well electrodes.

The reservoir is filled with the halide-containing electrolytic buffer solution, and the solution displacement block is inserted in the reservoir. The solution displacement block forces halide-containing electrolytic buffer solution through the narrow channel into the lens well(s), so as to completely fill the channel and to immerse the contact lens or lenses contained in the lens well(s).

The halide-containing electrolytic buffer solution may contain any alkali or alkaline earth halide compounds such as NaCl, KCl, KBr, NaBr, etc. The electrolytic buffer solution is preferably a borate, phosphate or physiologically compatible buffer saline. The solution may contain a preservative as an optional ingredient. A protein removal agent may also be added to improve cleaning efficacy.

In the first step, a unidirectional electric field is generated in the halide-containing electrolytic solution by application of a potential voltage to the two electrodes, so that the two electrodes have an opposite polarity. Preferably, the polarity and potential applied to the electrodes is set according to a predetermined program of the control means.

The electric field causes the generation of the halogen from the halide in the lens well or wells. The electric field is maintained for a duration of time until a disinfecting concentration of the halogen is generated and until the lenses are disinfected. If a predetermined program is used, the duration of this step may be predetermined and set.

Then, the polarity of the electrodes is changed, so that the two well electrodes have a negative charge, and the reservoir electrode has a positive charge. This causes the reconversion of the halogen back to the halide. This step is maintained until the concentration of the halogen is substantially reduced or eliminated, so that the contact lenses need not be rinsed before inserting them into the eyes of the user. If a predetermined program is used, the initiation of this step, its duration, and the potential applied to the electrodes, may be predetermined and set.

Between the disinfection and neutralization steps, there may be another step whereby the polarity of the two lens electrodes is reversed and opposite from each other. This step causes the generation of a further amount of halogen, and the step helps better clean the surfaces of the lens well electrodes.

One of ordinary skill in the art will recognize that the same essential results of the present invention may be obtained by the application of different sequences of polarities to the various electrodes depending upon the timing sequence, etc., as well as by the application of different voltages and durations. These scenarios are intended to be fully covered by the present invention.

The following table summarizes typical operating conditions of the lens care system of the present invention and possible ranges of the operating conditions:

| Typical Operating Conditions | |
| --- | --- |
| Time for step 1 (disinfection) | 2 seconds |
| Time for step 2 (neutralization) | 10 minutes |
| Voltage of steps 1 and 2 | 6 V |
| Concentration of $Cl_2$ generated at end of step 1 | 80 ppm |
| Final $Cl_2$ concentration at end of step 2 | less than 3 ppm |
| Possible Ranges for Operating Conditions | |
| Time for step 1 (disinfection) | 1 sec. to 10 minutes |
| Time for optional disinfection step between steps 1 and 2 | 0 to 20 minutes |
| Time for step 2 (neutralization) | 2 to 40 minutes |
| Voltage of steps 1 and 2 | 1.0 V to 9 V |
| Voltage for optional step | 0 V to 6 V |
| Concentration of $Cl_2$ generated at end of step 1 | at least 10 ppm |
| Final $Cl_2$ concentration at end of step 2 | less than 3 ppm |

Examples 1-6

Using a device of the present invention according to FIGS. 5A-C, two soft contact lenses were placed in respective lens wells 4. The lens wells 4 and reservoir 7 were filled with a borate buffer saline solution. The top was placed on the housing and the electrodes were connected to the controller.

The controller which was used had the capability of supporting different voltages of from 0.0 V to 9.0 V and different polarities (+ or -). The controller also had at least three different output voltages and variable timing for every event requirement.

The device used could be provided with a rechargeable battery, and it could be programmed to operate under battery voltage conditions.

The specific settings of the controller concerning the potential voltage, polarity of the electrodes, and duration of each step, for each of Examples 1-6 are summarized in Table 1 below.

At the end of the whole process, the residual chlorine in the lens wells 4 was evaluated by a spectrophotometric method. The results for each example are shown in Table 1.

EXAMPLE 7

The procedure of Example 1 was duplicated, except that the time of event programming was lengthened, and the buffer solution employed was SOFTWEAR (TM), which contains 50-60 ppm hydrogen peroxide in a borate buffer saline. The residual chlorine is shown in Table 1.

From the foregoing results, it is demonstrated that the concentration of the halogen which can be generated by the method and device of the present invention reaches a very high level in a very short period of time. Thus, the disinfection time is very short. The halogen concentration may also be easily controlled by time and voltage.

Further, the overall time required for the entire process is quite short in comparison to the time required in conventional disinfecting methods and apparatuses.

Furthermore, by the construction and operation of the present device, the concentration of the disinfecting agent is essentially eliminated. And by the use of a halide-containing electrolytic buffer solution, the solution maintains a neutral pH (7.0+0.5). Therefore, rinsing of the contact lenses after cleaning is not required.

TABLE 1

| Example | Step | Potential (V) | Polarity of Electrode | | | | | Time | Residual Chlorine | Buffer Saline |
|---|---|---|---|---|---|---|---|---|---|---|
| | | | 1 | 2 | 3 | 1a | 2a | | | |
| 1 | 1 | 6 | − | + | 0 | − | + | 2 sec | 0.4 ppm | Borate |
| | 2 | 6 | − | − | + | − | − | 10 min | | |
| 2 | 1 | 6 | − | + | 0 | − | + | 2 sec | 2.0 ppm | Borate |
| | 2 | 0 | | | | | | 10 min | | |
| | 3 | 6 | − | − | + | − | − | 10 min | | |
| 3 | 1 | 6 | − | + | 0 | − | + | 2 sec | 0.3 ppm | Borate |
| | 2 | 6 | − | − | + | − | − | 20 min | | |
| 4 | 1 | 3 | − | + | 0 | − | + | 5 sec | 0.1, 0.3 ppm | Borate |
| | 2 | 6 | − | − | + | − | − | 20 min | | |
| 5 | 1 | 3 | − | + | 0 | − | + | 5 sec | 1.0 ppm | Borate |
| | 2 | 3 | + | − | 0 | + | − | 5 sec | | |
| | 3 | 6 | − | − | + | − | − | 20 min | | |
| 6 | 1 | 3 | − | + | 0 | − | + | 10 sec | 0.2 ppm | Borate |
| | 2 | 6 | − | − | + | − | − | 20 min | | |
| 7 | 1 | 3 | − | + | 0 | − | + | 3 min | 1.1, 3.4 ppm | SOFTWEAR ™ |
| | 2 | 6 | − | − | + | − | − | 20 min | | |

It will be understood by those skilled in the art that various other arrangements than those described herein will occur to those skilled in the art, which arrangements are within the scope and spirit of the present invention. It is, therefore, to be understood that the invention is not intended to be limited to the specific embodiments disclosed herein but is extended to obvious variations and equivalents thereto.

I claim:

1. A contact lens care device for cleaning and disinfecting contact lenses, which comprises:
   a housing;
   a first well disposed within said housing defining a cavity for holding a halide-containing electrolytic buffer solution, said first well having two opposed electrodes disposed therewithin, said two opposed electrodes being spaced apart for receiving a contact lens therebetween;
   a reservoir disposed within said housing defining a cavity for holding a halide-containing electrolytic buffer solution, said reservoir having an electrode disposed therewithin;
   an ion permeable bridge connecting said first well and said reservoir; and
   a control means operatively connected to said two opposed electrodes of said first well and said reservoir electrode for controlling a potential voltage applied to said electrodes and for generating an electrical field between said electrodes.

2. A contact lens care device according to claim 1, further comprising a second well disposed within said housing defining a cavity for holding a halide-containing electrolytic buffer solution, said second well having two opposed electrodes disposed therewithin, said two opposed electrodes being spaced apart for receiving a contact lens therebetween, said second well and said reservoir being connected by an ion permeable bridge, and said two opposed electrodes of said second well being operatively connected to said control means.

3. A contact lens care device according to claim 2, wherein said first and second wells are connected so that the solutions contained within said wells may intermix.

4. A contact lens care device according to claim 2, wherein said first and second wells are isolated so that the solutions contained within said wells may not intermix.

5. A contact lens care device according to claim 1, wherein said first well includes a lens holding means.

6. A contact lens care device according to claim 5, wherein said lens holding means is a lens basket.

7. A contact lens care device according to claim 5, wherein said lens holding means are the opposed surfaces of said two opposed electrodes of said first well which are shaped in complementary convex and concave configurations.

8. A contact lens care device according to claim 2, wherein said second well includes a lens holding means, and said lens holding means are the opposed surfaces of said two opposed electrodes of said second well which are shaped in complementary convex and concave configurations.

9. A contact lens care device according to claim 1, wherein said ion permeable bridge is a narrow channel, and further comprising a solution displacement block removably insertable within an upper portion of said reservoir.

10. A contact lens care device according to claim 1, wherein said two opposing electrodes of said first well are spaced apart about 3/16's of an inch.

11. A contact lens care device according to claim 2, wherein said two opposing electrodes of said second well are spaced apart about 3/16's of an inch.

12. A contact lens care device according to claim 1, wherein said control means is a controller device which is preprogrammed to automatically control the applied potential voltage and polarities of said electrodes of said first well and said reservoir.

13. A contact lens care device according to claim 2, wherein said control means is a controller device which is preprogrammed to automatically control the applied potential voltage and polarities of said electrodes of said first and second wells and said reservoir.

14. A contact lens care device comprising a housing, at least one well therein for immersing and cleaning or disinfecting a contact lens, said well containing at least one electrode disposed therewithin, a reservoir within said housing containing at least one electrode and connected to said well by a channel ion permeable bridge, and a control means operatively connected to said electrodes, said control means and said housing being separate units operatively connected to each other by cable or by a detachable arrangement.

15. A contact lens care device according to claim 14, wherein said detachable arrangement of said control means and said housing comprises an interlocking arrangement of said control means and said housing.

16. A contact lens care device according to claim 14, wherein said detachable arrangement of said control means and said housing comprises said control means being removable from and insertable into said housing.

17. A contact lens care device according to claim 14, wherein said detachable arrangement of said control means and said housing comprises said housing being removable from and insertable into said control means.

18. A method of cleaning and disinfecting contact lens, which comprises the steps of:
immersing a contact lens in a halide-containing electrolytic buffer solution,
establishing an electric field in the halide-containing electrolytic buffer solution to generate the formation of halogen from the halide,
maintaining field until the contact lens is disinfected and cleaned,
changing the electric field to convert the halogen back to halide, and
maintaining the electric field until substantially all of the halogen is converted back into the halide.

19. A method of cleaning and disinfecting contact lens according to claim 18, wherein the contact lens is immersed in a lens well disposed within a housing defining a cavity for holding the halide-containing electrolytic buffer solution, the lens well having two opposed electrodes disposed therewithin, and the two opposed electrodes being spaced apart for receiving a contact lens therebetween; the housing having a reservoir disposed within the housing defining a cavity for holding a halide-containing electrolytic buffer solution, the reservoir having an electrode disposed therewithin; the housing having an ion permeable bridge connecting the lens well and the reservoir; and the housing having a control means operatively connected to the two opposed electrodes o the lens well and the reservoir electrode for controlling a potential voltage applied to the electrodes and for generating an electrical field between the electrodes.

20. A method of cleaning and disinfecting contact lens according to claim 18, wherein the ion permeable bridge is a narrow channel, and wherein the contact lens is immersed by filling the reservoir with the halide-containing displacement block in an upper portion of the reservoir, thereby forcing the halide-containing electrolytic buffer solution into the lens well through the narrow channel.

21. A method of cleaning and disinfecting contact lens according to claim 18, wherein the electric field is established in the halide-containing electrolytic buffer solution to generate the formation of halogen from the halide by applying potential voltages to the two opposing electrodes of the lens well such that the electrodes have an opposite polarity.

22. A method of cleaning and disinfecting contact lens according to claim 18, wherein the established electric field is reversed during the step where the halogen is being formed, by reversing the polarities of the opposing lens well electrodes, so that additional halogen is formed in the well and the electrode surfaces are cleaned of contaminants.

23. A method of cleaning and disinfecting contact lens according to claim 18, wherein the electric field is changed in the halide-containing electrolytic buffer solution to convert the halogen back to the halogen, by applying potential voltages to the two opposing electrodes of the lens well so that both electrodes have negative polarities, and by applying a potential voltage to the reservoir electrode so that the electrode has a positive polarity.

24. A method of cleaning and disinfecting contact lens according to claim 18, wherein the control means is preprogrammed to automatically control the duration, applied potential voltages and polarities of the electrodes of the well and the reservoir during each process step.

25. A contact lens care device comprising a housing, at least one well therein for immersing and cleaning or disinfecting a contact lens, said well containing at least one electrode disposed therewithin, a reservoir within said housing containing at least one electrode and connected to said well by a channel ion permeable bridge, a control means operatively connected to said electrodes, and a solution displacement block removably insertable within an upper portion of said reservoir, wherein said well is filled with a cleaning solution by filling the reservoir with solution and inserting the solution displacement block into the upper portion of said reservoir, thereby forcing solution through the channel into said well.

* * * * *